United States Patent
Tirosh et al.

(10) Patent No.: US 6,200,962 B1
(45) Date of Patent: Mar. 13, 2001

(54) THIONOPHOSPHATE DERIVATIVES, PROCESS FOR THEIR PREPARATION AND PHARMACEUTICAL COMPOSITIONS CONTAINING THEM

(75) Inventors: Oren Tirosh; Joshua Katzhendler; Isaac Ginsburg; Yehezkel Barenholz; Ron Kohen, all of Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 08/849,122

(22) PCT Filed: Nov. 13, 1995

(86) PCT No.: PCT/US95/15199

§ 371 Date: Aug. 7, 1997

§ 102(e) Date: Aug. 7, 1997

(87) PCT Pub. No.: WO96/16663

PCT Pub. Date: Jun. 6, 1996

(30) Foreign Application Priority Data

Nov. 28, 1994 (IL) .................................................. 111797

(51) Int. Cl.[7] ............................ A61K 31/664; A61P 39/06
(52) U.S. Cl. .............................................. 514/129; 558/177
(58) Field of Search ................................ 514/129; 558/177

(56) References Cited

U.S. PATENT DOCUMENTS

| | | | |
|---|---|---|---|
| 2,995,596 | * | 8/1961 | Debo ..................... 558/177 |
| 3,087,955 | * | 4/1963 | Brust ..................... 558/199 |
| 3,251,675 | * | 5/1966 | Senkbeil ............... 558/199 X |
| 3,337,656 | * | 8/1967 | Curtis et al. .......... 558/199 |
| 3,531,550 | * | 9/1970 | Herber et al. ......... 564/14 X |
| 3,597,476 | | 8/1971 | Edwards et al. ...... 260/551 |
| 3,670,057 | | 6/1972 | Tsuchiya et al. . |
| 3,702,332 | | 11/1972 | Pillon et al. .......... 260/347.7 |

FOREIGN PATENT DOCUMENTS

964678 * 5/1957 (DE) .

OTHER PUBLICATIONS

Chemical Abstracts vol. 53, No. 14937a; DE 964678, abstract, 1959.*

(List continued on next page.)

Primary Examiner—Michael G. Ambrose
(74) Attorney, Agent, or Firm—Kohn & Associates (57) ABSTRACT

The invention relates to a compound of formula (I)

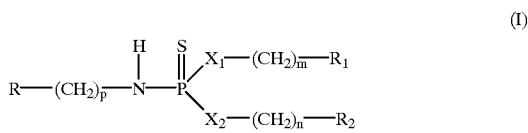

(I)

in which $X_1$ and $X_2$ each independently represents an oxygen or nitrogen atom; p,m and n are each independently an integer of at least 2; R, $R_1$ and $R_2$ each independently represents a hydrogen atom; a halogen atom; an optionally substituted straight-chained or branched alkyl alkenyl or alkynyl radical; a group $R_3O$ in which $R_3$ is hydrogen atom, an optionally substituted straight-chained or branched alkyl alkenyl or alkynyl radical; optionally substituted acyl or optionally substituted aryl or heteroaryl; a group $R_4O(O)C$ in which $R_4$ is a hydrogen atom or an optionally straight-chained or branched alkyl, alkenyl or allkynyl radical; a group —$SR_5$ is a hydrogen atom or an optionally substituted straight-chained or branched alkyl alkenyl or alkynyl radical; a group —$NR_6R_7$ in which $R_6$ and $R_7$ each independently represents a hydrogen atom, an optionally substituted straight-chained or branched alkyl, alkenyl or alkynyl radical; optionally substituted acyl; or an optionally substituted phosphate ester group. The invention also relates to processes., for The preparation of compounds of the formula and to pharmaceutical compositions containing the same.

2 Claims, 7 Drawing Sheets

OTHER PUBLICATIONS

Dean et al., 1991, Free radical damage to proteins: the influence of the relative localization of radical generation, antioxidants, and target proteins. *Free Radical Biol Med.* 11:161–168.

Ginsburg et al., 1993. Chemiluminesicence in activated human neutrophils. *Inflammation* 17:227–243.

Ginsburg et al., 1992, Synergism among oxidants, proteinases, phospholipases, micobial hemolysins, cationic proteins, and cytokines *Inflammation* 16:519–538.

Halliwell, 1990. How to characterize a biological antioxidant. *Free Radl Res. Comm.* 9:1–21.

Halliwell et al., 1987. Deoxyribose method: a simple "test–tube" assay for determination of rate constants for reactions of hydroxyl radicals. *Analyt. Biochem* 165:215–219.

Halliwell and Gutteridge, 1989. Free radicals in biology and medicine. *Free Radical in Biol. and Med. Clarendon Press (London)* 1–5.

Hazell and Stocker, 1993. Oxidation of low–density lipoprotein with hypochlorite causes transformation of the lipoprotein into a high–uptake form for macrophages. *Biochem J.* 290:165–172.

Heinecke et al., 1993. Oxidation of low density lipoprotein by thiols: superoxide–dependent and –independent mechanisms. *J. Lipid Res.* 34:2051–2061.

Ingold et al., 1993. Autoxidation of lipids and antioxidtion by α–tocopherol and ubiquinol in homogeneous solution and in aqueous dispersions . . . *Proc. Natl. Acad. Sci. USA* 90:45–49.

Jackson et al., 1993. Antioxidants: a bilogical defense mechanism for the prevention of atherosclerosis. *Med. Res. Rev.* 13:161–182.

Johnston, Jr. et al., 1975. The role of superoxide anion generation in phagocytic bactericidal activity. *J. Clin. Invest.* 55:1357–1370.

Kelner et al., 1990. Thioureas react with superoxide radicals to yield a sulfhydryl compound. *J. Biol. Chem.* 265:1306–1311.

Lichtenberg and Barenholz, 1988. Methods of biochemical analysis. *Methods of Biochem. Anal.* 33:337–462.

McCord and Fridovich, 1969. Enzymic function of erythrocuprein (hemocuprein). *J. Biol. Chem.* 244:6049–6055.

Neuzil et al., 1993. Radical–induced chain oxidation of proteins and its inhibition by chain–breaking antioxidants. *Biochem* 293:601–606.

Niki et al., 1984. Inhibition of oxidation of methyl linoleate in solution by vitamin E and vitamin C. *J. Biol. Chem.* 259:4177–4182.

Rice–Evance and Diplock, 1993. Current status of antioxidant therapy. *Free Rad. Biol. Med.* 15:77–96.

Steinberg et al., 1989. Modifications of low–density lipoprotein that increase its atherogenicity. *N. Eng. Med.* 320:915–923.

Guo et al., "N–substituted–O,O–diethylphosphoramidothioates" Chemical Abstracts, vol. 121, No. 9 (1994), No. 109001.

Kas'Yanova E F et al., "Synthesis of some derivatives of monothiophosphoric acid for the flotation of ores of heavy nonferrous metals" Chemical Abstracts, vol. 1, No. 1 (1969), No. 3242g.

Mandel'Baum Y A et al., "Reaction of phosphorus thio acid chlorides with ethanolamine" Chemical Abstracts, vol. 85, No. 17 (1976), No. 123267.

Tirosh O et al.,"Antioxidant properties of amidothionophosphates: novel antioxidant molecules" Free Radical Biol. Med., vol. 20(3):421–32 (1996) XP–002055303.

* cited by examiner

THIONOPHOSPHATE DERIVATIVES, PROCESS FOR THEIR PREPARATION AND PHARMACEUTICAL COMPOSITIONS CONTAINING THEM

This applications is a 371 of PCT/US95/15199 Nov. 13, 1995.

FIELD OF THE INVENTION

The invention relates to novel thionophosphate organic derivatives, their preparation and pharmaceutical compositions containing them, particularly suitable for treating and/or preventing oxidative damage.

BACKGROUND OF THE INVENTION

Reactive Oxygen Species (ROS) have been proposed to cause oxidative damage to biological molecules and to be involved in the development of many severe human disorders i.e., atherosclerosis, cancer, rheumatoid artritis and inflammation [Halliwell, B., and Gunteridge, J. M. C. (eds.) (1989) Free Radical in Biology and Medicine, Clarendon Press, London. Neuzil, J., et al. (1993) Biochem. J. 293:601–606; Sies, H., (ed.) (1985) Oxidative stress, Academic Press, London: Steinberg, D. et al. (1989) New Engl. J. Med. 320:915–923].

The antioxidants defense system is composed of several lines of defense. These lines of defense include macromolecular molecules (mainly enzymes such as superoxide dismutase (SOD), catalase glutathione peroxidase and other protecting enzymes) and low molecular weight antioxidants [Halliwell. B. (1990) Free Rad. Res. Comm. 9:1–327].

Despite intensive clinical trials using antioxidants, only marginal therapeutic and preventive successes have been reported [Rice-Evance. C. A., and Diplock A. T. (1993) Free Radical Biology & Medicine 15:77–96]. There are several reasons for the limited success in the use of antioxidants therapy:

1) Antioxidants can be classified according to their partition between aqueous and lipid compartments (lipoproteins and membranes) [Dean. R. T. et al. (1991) Free Radical Biology &, Medicine 11:161–168; Niki. E. et al. (1984) J. Biol. Chem. 259:4177– 4182]. Most of the natural antioxidants cannot cross biological membranes and cannot move freely by spontaneous diffusion between aqueous and lipid environments. Some of them are ionized at natural physiologic pH, a fact that also restricts their movement.

2) Antioxidants should not have any pro-oxidative effects, i.e. thiols group produced superoxide radicals causing LDL oxidation and NO. radical distraction or ascorbic acid that induced free radical production when coupled with a transition metal [Heinecke, J. et al. (1993) J. Lipid Res. 34:2051–2061; Jackson, R. L., et al. (1993) Medicinal Research Reviews 13:161–182; Ingold, K. U., et al. (1993) Proc. Natl. Acad. Sci. USA 90:45–49];

3) Halliwell (ibid.) clarified that essential antioxidants should possess a broad spectrum of ROS scavenging capacities and should be in close proximity to the biological target and at relatively high concentrations.

N,N'-dimethyl thiourea (DMTU) is a well known antioxidant and a potent hydroxyl radical scavenger, also capable of removing hydrogen peroxide and superoxide radicals [Kelner. M. J., et al. (1990) J. Biol. Chem. 265:1306–1311; Dey, G. R., et al. (1994) J. Chem. Soc. Perkin Trans 2:1625–1629]. Notwithstanding their antioxidative properties, various DMTU-derived compounds are relatively highly toxic (e.g., lung, liver and thyroid toxicity) and considered carcinogenic substances.

Thus, antioxidants which can fulfill the requirements mentioned above may serve as efficient molecules capable of coping with oxidative stress and may thus be good candidates for antioxidative therapy. There is a basic need for better antioxidants in order to prevent the tissues natural deterioration and to prevent inflammatory and other tissue damage caused by reactive oxygen species.

The present invention thus relates to novel compounds which are efficient, non-toxic, therapeutic antioxidants.

SUMMARY OF THE INVENTION

The present invention relates to compounds of the general formula:

(I)

in which $X_1$ and $X_2$ each independently represents an oxygen or nitrogen atom; p, m and n are each independently an integer of at least 2; R, $R_1$ and $R_2$ each independently represents a hydrogen atom; a halogen atom; an optionally substituted straight-chained or branched alkyl, alkenyl or alkynyl radical; a group $R_3O$ in which $R_3$ is a hydrogen atom, an optionally substituted acyl group or an optionally substituted straight-chained or branched alkyl, alkenyl or alkynyl radical; optionally substituted aryl or heteroaryl; a group $R_4O(O)C$ in which $R_4$ is a hydrogen atom or an optionally substituted straight-chained or branched alkyl, alkenyl or alkynyl radical; a group $-SR_5$ in which $R_5$ is a hydrogen atom or an optionally substituted straight-chained or branched alkyl, alkenyl or alkynyl radical; a group $-NR_6R_7$ in which $R_6$ and $R_7$ each independently represents a hydrogen atom, an optionally substituted straight-chained or branched alkyl, alkenyl or alkynyl radical; optionally substituted acyl; or an optionally substituted phosphate ester group.

The invention also relates to a process for the preparation of a compound of formula I comprising reacting a dialkyl halothiophosphate of the formula (II)

in which A is a halogen atom selected from chlorine, bromine and iodine and $X_1$, $X_2$, $R_1$, $R_2$, m and n are as defined above with an amine of the formula (III)

in which R and p are as defined above.

The invention further relates to pharmaceutical compositions comprising as active ingredient at least one compound of formula I in a suitable pharmaceutically acceptable carrier or diluent. The pharmaceutical compositions of the invention are particularly suitable for preventing and/or treating oxidative damage associated with inflammatory disorders, atherosclerosis, ischemia, traumatic shock, degenerative brain disease, skin disorders, septic shock, lung disease, malignant disease, damages caused by ionizing or non-ionizing radiation and poisonings by xanobiotics which generates reactive oxygen species.

In a further embodiment the invention relates to methods of preventing and/or treating oxidative damage in a patient in need of such treatment by administering to said patient a therapeutically effective amount of at least one compound of formula I or of a pharmaceutical composition according to the invention In yet a further aspect the invention relates to antioxidative additives comprising as active ingredient at least one compound of formula I in a suitable carrier or diluent.

BRIEF DESCRIPTION OF THE FIGURES

FIG. 1

Structure of compounds A, B and C.

FIG. 2

$^{31}$P NMR spectra of SW liposomes (125 mM) with compound B (5 mM).

Two singlets were monitored one at 0.467 ppm represents the phosphatidylcholine typical chemical shift and the second at 73.09 ppm represents the compound B molecules chemical shift.

FIG. 3

$^{31}$P NMR spectra of compound B (5 mM) following exposure to oxidative stress, of sodium hypochlorite (6 mM).

NMR spectra were recorded immediately following the oxidative stress. One single peak was monitored at 9.28 ppm.

FIG. 4

$^{31}$P NMR spectra of compound B (5 mM) following exposure to oxidative stress of hydrogen peroxide (100 mM). NMR spectra were recorded 11 h following the oxidative stress. Two singlet peaks were monitored at 9.16 ppm and at −3.55 ppm.

FIG. 5

$^{31}$P NMR kinetic measurements of compound B (5 mM) reaction with hydrogen superoxide (100 mM) in two different environments—dioxane:water 1:9 dielectric constant 72.63 and dioxane:water 9:1 dielectric constant 9.58.

FIG. 6

Hydroxyl radical scavenging by compound C

Deoxyribose degradation in the presence of various concentrations of AMTP was followed as described under Materials and Methods using a final deoxyribose concentration of 18 mM in the reaction mixture.

FIG. 7

Effect of increasing concentration of compound B on NTA-$Fe^{2+}$ chelate (5 mM), $H_2O_2$ (10 mM) and HRP (18 units/ml) chemiluminescence.

The results represent a typical experiment performed on the same day.

FIG. 8

Concentration dependent scavenging rate of superoxide radicals by increasing concentration of compound B detected spectrophotometrically by following the reduction of cytochrome C.

FIG. 9

Thiobarbituric acid reactive species evaluation in 1% commercial intra lipid emulsion following exposure to oxidative stress of vitamin C (100 μM). Ferrous ammonium sulfate (IOOmmM) and $H_2O_2$ (1 μM), with and without AMTP molecules, as shown. Concentrations were Compound A (10 mM), Compound B (10 mM) and Compound C (10 mM).

FIG. 10

Lipid Hydroperoxides evaluation in partially oxidized SWV liposomes (12.5 mM incubated with (5 mM) AMTP molecules at room temperature.

Lipid Hydroperoxide was measured as described under Materials and Methods after 2, 4, 10 and 24 hours incubation time. Control, compound A, compound B and compound C, as shown.

FIG. 11

NaOCl mediated loss of BSA's tiyptophan fluorescence intensity with and without various ceoncentrations of AMTP molecules and cystine. Control, compound A, compound B, compound C and cystine are as shown. The BSA (0.5 mg/kg) was oxidized with NaOCl (1 mM) and the unmodified tryptophan was quantitated by fluorescence. The results are the average of three experiments.

FIG. 12

NaOCl mediated loss of BSA's cyteine residues with and without various concentrations of AMTP molecules.

Control, compound A, compound B, and compound C are as shown. The BSA (0.5 mg/kg) was oxidized with NaOCl (1 mM) and the unmodified cysteine was quantitated by DTNB reaction. The results are the average of three experiments.

FIG. 13

Effect of compound B on chemiluminescence generated by PMNs stimulated by; cationized streptococci.

PMNs Control 1 ($3*10^5$) or control 2 ($1.5*10^6$) were stimulated by cationized streptococci in the presence of various concentrations of compound B and 2 mM DMTU. Control 1, compound B (0.2 mM), compound B (0.5 mM), compound B (1 mM), Control 2, compound B (2 mM), Compound B (4 mM) Compound B (6 mM), Compound B (8 mM) and DMTU (2 mM) are as shown.

FIG. 14

Effect of streptolysin S (SLS) and glucose oxidase (GO) (0.5units/ml)—generated Hydrogen peroxide on the killing of human fibroblast cells in culture and the protective effects of AMTP molecules at various concentrations. DMTU and catalase. Control, Compound A, Compound B, Compound C, DMTU and catalase are as shown.

DETAILED DESCRIPTION OF THE INVENTION

The present invention relates to compounds of the general formula:

(I)

$$R-(CH_2)_p-\overset{H}{\underset{}{N}}-\overset{S}{\underset{}{P}}\begin{matrix}X_1-(CH_2)_m-R_1\\X_2-(CH_2)_n-R_2\end{matrix}$$

in which $X_1$ and $X_2$ each independently represents an oxygen or nitrogen atom; p, m and n are each independently an integer of at least 2; R. $R_1$ and $R_2$ each independently represents a hydrogen atom; a halogen atom; an optionally substituted straight-chained or branched alkyl, alkenyl or alkynyl radical; a group $R_3O$ in which $R_3$ is a hydrogen atom, an optionally substituted acyl group or an optionally substituted straight-chained or branched alkyl, alkenyl or alkynyl radical; optionally substituted aryl or heteroarvl; a group $R_4O(O)C$ in which $R_4$ is a hydrogen atom or an optionally substituted straight-chained or branched alkyl, alkenyl or alkynyl radical; a group $-SR_5$ in which $R_5$ is a hydrogen atom or an optionally substituted straight-chained or branched alkyl, alkenyl or alkynyl radical; a group $-NR_6R_7$ in which $R_6$ and $R_7$ each independently represents a hydrogen atom, an optionally substituted straight-chained or branched alkyl, alkenyl or alkynyl radical; optionally substituted acyl; or an optionally substituted phosphate ester group.

The various alkyl, alkenyl, alkynyl, acyl, aryl and heteroaryl radicals and groups can be optionally subsituted by one or more substitutents which may be selected from alkyl, alkenyl, alkynyl, alkoxy, alkenyloxy, acyl, acyloxy, ether, ester, halogen, phosphate, amino, amido, thio, lipid, phospholipid, peptide, vitamin and other suitable substitutents.

Preferred compounds of formula I are those in which $X_1$ and $X_2$ are both oxygen, $R_1$ and $R_2$ are both alkyl, preferably lower alkyl such as ethyl, and p, m, and n are 2. Particularly preferred such compounds are those in which R is an alkyl, hydroxy or carboxy group.

The invention also relates to a method for the preparation of compounds of formula I. comprising reacting a dialkyl halothiophosphate of the formula (II)

in which A is a halogen atom selected from chlorine, bromine and iodine and $X_1$, $X_2$, $R_1$, $R_2$, m and n are as defined above with an amine of the formula (III)

in which R and p are as defined above.

Compounds of formula II in which said halogen atom is chlorine are preferred starting materials.

The method of the invention is expemlified in more detail in the following Preparatory Examples.

Figure 1A:
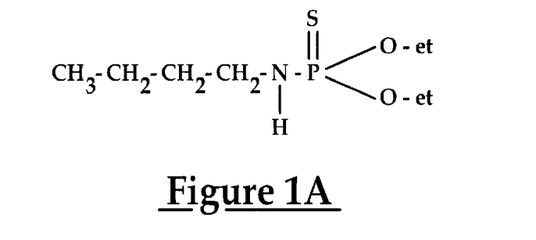
Figure 1B:
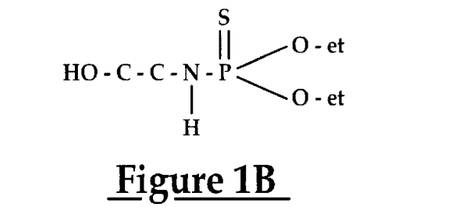
Figure 1C:
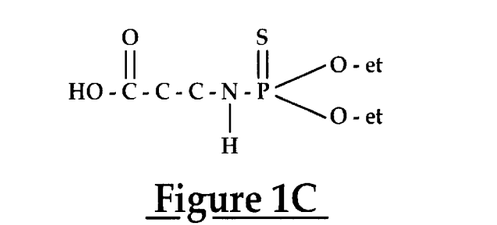

The basic chemical structure of the compounds of the invention includes the group $-P-N=S$, which resembles the thiourea $-N-C=S$ core, in which the central carbon atom has been replaced by a phosphorus atom, to give $-N-P=S$, which is the characteristic functional group the novel compounds of the invention. This functional group is based on a primary amido thionophosphate (AMTP) chemical bond. The specific compounds shown in FIG. 1, which are only representative of the numerous possible compounds, differ in their $oil_{(mineral)}$/water and octanol/water partitioning:

$P_A$(oil/water)=4.82; $P_A$(octanol/water)=6.14; $P_B$(oil/water)= 0.25;

$P_B$(octanol/water)=3.22; $P_C$(oil/water)=0.39;

$P_C$(octanol/water)=0.44.

Another unique property of the new ATMP functional group in the compounds of the invention, is that the thionophosphate group can be monitored by 31P NMR. The typical chemical shift of an AMTP molecule is about 72 ppm, which differs from other biological phosphates (FIG. 1). This unique property makes the tracing and examination of these compounds very simple.

The compounds of the invention have been shown to be capable of scavengzing different types of oxidants including, for example, hydrogen peroxide ($H_2O_2$), sodium hy,pochlorite (NaOCl), hydroxyl radical (OH.) and superoxide radical ($O_2^-$.). Thus, these new compounds are capable of protecting relevant biological molecules such as proteins against various kinds of oxidative stress. In addition, the compounds of the invention have been shown to have no prooxidative effects in comparison to other known antioxidants. Moreover, the compounds of the invention are also capable of coping with activated neutrophils and to protect cell cultures against synergistic killing by $H_2O_2$ and streptolysin S, a combination which serves as a model for tissue damage. Furthermore, the toxicity of the new AMTPs has been tested and they are expected to be suitable for administration into animals at the relatively high doses needed to cope with oxidative stress. These properties of the novel compounds of the invention will now be discussed in more detail on hand of the following Examples and appended Figures.

As stated, the novel organic thionophosphates of the invention are capable of reacting with hydroxyl radical, sodium hypochlorite, hydrogen peroxide, superoxide and lipid hvdroperoxide. While the compounds of the invention are not capable of inhibiting lipid peroxidation by free radical chain breaking, neither scavenging peroxyl radicals, they can limit lipid peroxidation to a certain degree by preventing the initiation phase through the scavenging of hydroxyl radicals. Estimation of rate constants of AMTPs shows that by the scavenging mechanism they can prevent hydroxyl radical damage to biological systems, and that they are also capable of removing the less reactive ROS ($H_2O_2$, $O_2$.—) that can lead to hydroxyl radical production.

Figure 3:
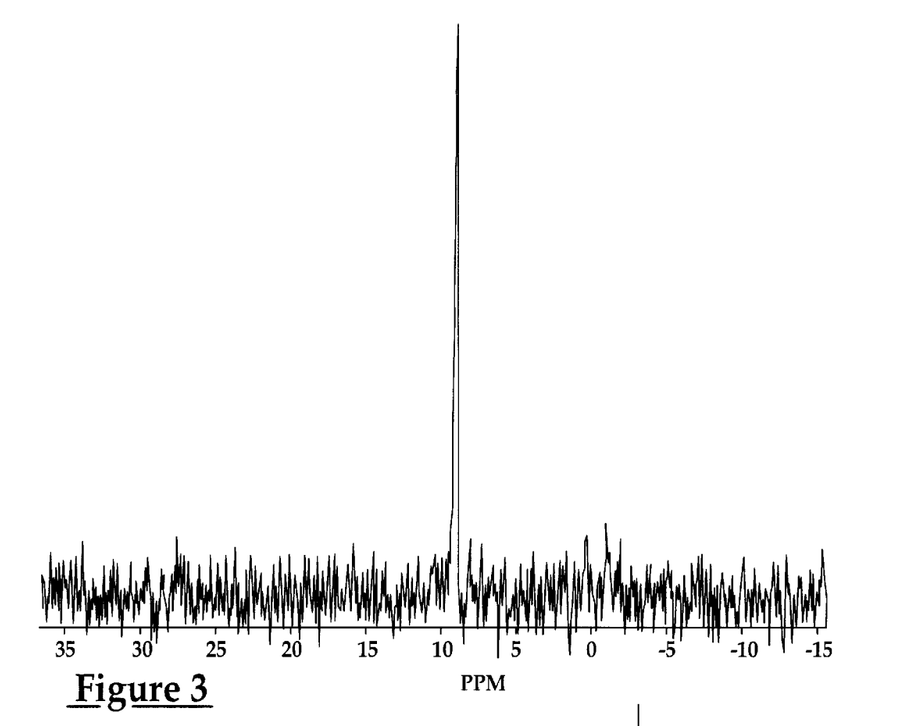

The compounds of the invention are extremely efficient scavengers of sodium hypochlorite, an oxidant produced by neutrophils at the site of inflammation and was recently shown by Stocker et al. [ibid.] to increase LDL uptake bv macrophages and to cause protein damage to apo B 100. [FIG. 3]. The compounds of the invention also inhibit the flux of oxygen free radicals from activated neutrophils, a finding that has implications on the prevention of synergistic cell damage in inflamed tissues [Ginsburg et al. (1992) ibid.]. The compounds of the invention were used to prevent synergistic killing of cell cultures by $H_2O_2$ and streptolysin S. Compound B (Preparatory Example 2) (unionized) was much more efficient than compound C (Preparatory Example 3) (ionized) in preventing cell damage. The finding that the novel compounds react with hydrogen peroxide in a time scale of hours may indicate that they probably contributed to the survival of the cell cultures by hydroxyl radical scavenging from outside the cell (compounds B and C) and from the cell interior (compound B).

$^{31}P$ NMR showed that oxidized AMTPs have one to two major oxidation products that contain phosphorus. The products are very much similar to biological phosphates. The thionophosphates of the invention did not show acute toxicity to Sabra rats at 500 mg/kg.

An advantage of the novel thionophosphate molecules is that they can be designed to meet specific needs as antioxidants. Hence, they need not be limited by an ionized active group, as is the case with other antioxidants such as ascorbic acid. The lipophilicity of the compounds of the invention can be controlled, by varying the different subsituents on the thionophosphate core, they can be designed to move freely by spontaneous diffusion in different environments, and to cross biological barriers such as membranes, and targeted to specific organs.

Another advantage of the novel compounds is that they are incapable of reducing transition metals and oxygen, since they do not possess any pro-oxidative properties like conventional antioxidants.(Table 1). A cyclic voltmeter scanning up to 2 volts with glass carbon as a working electrode revealed no reducing power of these molecules, hence, no oxygen reduction to free radicals is possible. The novel compounds of the invention are superior to the thiourea family of molecules (which are also considered powerful antioxidants) because they lack the relatively high toxicity of the thiourea molecules (e.g., lung, liver and thyroid toxicity). Thus, for example α-naphthyl-thiourea has an $LD_{50}$ of about 10 mg/kg and DMTU is also considered a toxic compound [Boyd, M. R. and Neal, R. A. (1976) Drug Metabolism and Disposition 4:314].

In view of their above described properties, the compounds of the invention may be advantageously used in preventing and/or treating oxidative damage.

As mentioned above, oxygen free radicals are considered to be responsible for oxidative toxicity in mammals and the resulting biological damage. The production of oxygen reactive metabolites can occur in various systems such as mitochondria, phagocytes, liver Kupfer cells, monocytes, basophyls, eosinophyls and mast cells. In some genetic disorders, such as chronic granulomatosus disease (CGD), phaaocytes are incapable of producing the oxygen radicals and consequently patients suffer recurring infections which may lead to death [Johnston, Jr., R. B. et al. (1975) J. Clin. Invest. 55:1357]. Another source for free radicals are enzymes such as prolyl hydrolase, lipoxygenase and cycloxygenase, which during their catalytic activity produce oxygen free radicals [Halliwell and Gutteridge ibid.].

Amongst the diseases in which reactive oxygen species play a role in both initiation and pathogenesis, one can find chronic inflammation such as rheumatoid arthritis; sepsis; autoimmune diseases such as Hashimoto's thyroiditis, systemic lupus erythematosus, myastenia gravis, chronic autoimmune gastritis, dermatomyositis, etc.; degenerative brain diseases such as epilepsy, Parkinsonism, Wilson's disease and Alzheimer's disease; eye disease such as cataract and retinopathy; lung diseases such as Adult Respiratory Distress Syndrome (ARDS) and emphysema; malignant diseases; and age related disease such as amyloid generation, age pigmentation and neuronal damage. Of particular importance is the involvement of oxygen driven free radicals in the post-ischemic damage to various biological tissues such as heart and brain Exposure of humans to free radicals is not limited to the endogenous oxygen free radicals, but also to exogenous sources. Various substances which are xanobiotics producing reactive oxygen species, for examples agrochemicals like Paraquat™, can serve as free radical generation systems, causing poisonings. Other substances such as alloxan, isouramil, cigarette smoke, air pollutants, carcinogenic and mutagenic agents and many drugs, as well as ionizing and non-ionizing radiation, can also generate oxygen free metabolites and cause biological damage.

In view of their above described properties, the novel compounds of the invention are particularly useful for treating and or preventing the above pathological conditions. Thus, in yet a further aspect, the invention relates to pharmaceutical compositions comprising as active ingredient at least one compound of Formula (I), in a pharmaceutically acceptable carrier or diluent.

The pharmaceutical compositions of the invention may be particularly useful for preventing and/or treating oxidative damage associated with inflammatory disorders such as rheumatoid arthritis, atherosclerosis, post-ischemic brain and muscle damage, traumatic shock, degenerative brain disease such as Parkinson's disease and Alzheimer's disease, skin disorders such as eczema, pyodermes, dermatitis, allergies and urticaria, septic shock, lung disease, eye disease such as Adult Respiratory Distress Syndrome and emphysema, ionizing radiation damage, particularly skin and eye damage, eye diseases such as cataract and retinopathy, and malignant diseases.

The pharmaceutical composition of the invention may contain, in addition to the active ingredient, conventional pharmaceutically acceptable carriers, diluents and the like and may be prepared in any suitable dosage form. Such forms include solid compositions for oral administration such as tablets, capsules, pills and the like , which may be coated or otherwise compounded with pharmaceutically acceptable substances known in the art of pharmacy to provide a dosage form affording prolonged or sustained release. Liquid forms may be prepared for oral administration or for administration by injection, the term including sub-cutaneous, transdermal, intravenous, intra-muscular intratechal, etc. administration. The liquid compositions for oral administration may include aqueous solutions, flavoured syrups, aqueous or oil suspensions and the like. The liquid compositions may also be prepared in the form of eye drops and as aerosols for intra-nasal and like administration. Preparations in ointment or cream base are also envisaged.

The active dose for humans, as evident to the man versed in the art, would be determined by the attending physician in accordance with the disease to be treated or prevented, mode of administration, patient's age, sex, weight, counter indications and the like.

The invention further relates to a method of preventing and/or treating oxidative damage in a patient in need of such treatment by administering to said patient a therapeutically effective amount of at least one compound of formula I or of a pharmaceutical composition according to the invention.

The method of the invention may be particularly suitable for preventing and/or treating oxidative damage associated with inflammatory disorders such as rheumatoid arthritis, atherosclerosis, post-ischemic brain and muscle damage, traumatic shock, degenerative brain disease such as Parkinson's disease and Alzheimer's disease, skin disorders, septic shock, lung disease such as Adult Respiratory Distress Syndrome and emphysema, ionizing and non-ionizing radiation damage, particularly skin and eye damage, eye diseases such as cataract and retinopathy, malignant diseases and poisonings caused by xanobiotics which produce reactive oxygen species.

The various modes of administration have been described above.

In addition to their use as therapeutic agents, the compounds of the invention may be used as antioxidative additives, preventing deterioration of various food, cosmetic and other chemical industrial product due to oxidative damage. Thus, the invention further relates to an antioxidative additive comprising as active ingredient at least one compound of formula I in a suitable carrier or diluent.

While only few compounds will be described in detail on hand of the following Examples, these are illustrative only and do not in any sense limit the invention, which is only defined by the scope of the appended claims.

PREPARATORY EXAMPLES

Materials and Methods:

The various molecules synthesized in our laboratory were characterized by $^{31}P$ NMR, $^{1}H$ NMR FTIR TLC and element analysis. NMR spectra were recorded on a Varian Vxr 300S spectrometer. The $^{31}$P spectra were referenced to 1% $H_3PO_4$ in $D_2O$ which was used as an external standard. TLC was carried out on MERCK silica gel 60 $F_{254}$ precoated plates with different eluents (dichloromethane ethanol 95:5 for compound A and B or 80:20 for compound C respectively). The spots were developed by Molybdenum blue Sigma spray reagents for phosphor compounds, iodine vapor as a general detecting agent and ninhydrin 0.25% in ethanol for amines. FTIR spectra were recorded on a Perkin Elmer 2000-spectrometer.

Dichloromethane was refluxed with $P_2O_5$ for two hours and then distilled and stored over molecular sieves (4A).

All reagents for the synthesis were purchased from Aldrich.

Preparatory Example 1

Synthesis of n-butylamido diethylthioiiophosphate (Compound A): Diethyl chlorothiophosphate (2 gm/10.6 mmol) was dissolved in 50 ml dry dichloromethane. The solution was dropped for a period of 30 minutes into an ice cold stirred solution of 1-amino butane (3.86 cm/53 mmol) in 50 ml of dry dichloromethane. After one hour of stirring acidified water (HCl) (25 ml pH=2.0) was added and the organic layer was washed five times to extract all of the free amine. The organic layer was dried on anhydrous magnesium sulfate, filtered and evaporated to dryness. A clear yellow liquid was obtained: Yield: 2 gm (83.3%) $^{31}$P NMR (69.3 ppm single peak). IR: 1400,1490, 2900,3300. $^1$H NMR (300 MHz, CDCl3) d 0.85–0.95 (t,3H) d 1.25–1.4 (t,6H), d 1.4–1.45 (m,2H), d 1.45–1.65 (bd,2H), d 2.85–3 (bt,2H), d 3.95–4.15 (bq,4H).

Preparatory Example 2

Synthesis of 2-hydroxyamido diethyithionophosphate (Compound B): Diethyl chlorothiophosphate (2 gm/10.6 mmol) was dissolved in 50 ml dry dichloromethane and was dropped for a period of 30 minutes into an ice cold stirred solution of ethanol amine (3.2 gm/53 mmol ) in 50 ml of dry dichloromethane. After one hour of stirring, acidified water (HCl) 25 ml pH=2 was added and the organic layer was washed three times to extract all the free amine. The organic layer was dried on anhydrous magnesium sulfate, filtered and evaporated to dryness. A clear liquid was obtained: Yield :1.8 gm (79%) $^{31}$P NMR (72 ppm single peak). IR: 1400, 1490,2900,3500 (a broad peak). $^1$H NMR (300 MHz, CDCl3) d 1.25–1.35(t,6H), d3.03–3.13 (m,2H), d3.6–3.68 (t,2H),d 3.95–4.15 (bq,4H).

Preparatory Example 3

Synthesis of 2-carboxyamidodiethyl thionophosphate (Compound C): β-alanine (6.6 gm/74 mmol) was dissolved in 50 ml of water. Potassium hydroxide (3.56 gm/63.6 mmol) was added in small portions to the solution. The mixture was dried by lyophilization and was dissolved again in 100 ml hot DMF (130° C.). When the temperature dropped to 80° C., diethyl chlorothiophosphate (2 gm/10.6 mmol) in 50 ml of dry dichloromethane was dropped over a period of 30 minutes into the DMF mixture. After one hour of stirring, acidified water was added and the organic layer was washed three times to extract all the free amine from the organic layer. $^{31}$P NMR showed 82% purity of the compound (71 ppm). Yield: 1.9 gm (74%) IR: 1400, 1490,1700, 1750,2400,2900,3400. $^1$H NMR (300MHz,CDCl3) d1.4–1.6 (t,6H), d2.5–2.7(t,2H), d3.2–3.6 (m,2H), d3.8–4.2 (bq,4H).

Biological Experiments
Materials and Methods:

All reagents were purchased from Sigma Chemical Co. unless otherwise stated.

Toxicity study

The toxicity of compound B was tested by injecting 75 mg/kg, 150 mg/kg, 300 mg/kg, 500 mg/kg, 700 mg/kg and 1000 mg/kg i.p. to groups of eight Sabra mice. In addition, a repetitive i.p. injection of 75 mg/kg/day over a period of two weeks was conducted on eight mice. The mice were monitored for mortality and for chances in their weight compared to a saline injected control group.

$^{31}$P NMR spectra

ROS reaction with AMTP were recorded by $^{31}$P NMR spectra. $^{31}$P spectra were referenced to 1% $H_3PO_4$ in $D_2O$ and used as an external standard.

Hydroxyl radical deoxyribose assay

A modification of the assay described by Halliwell et al. [Halliwell, B. et al. (1987) Analyt. Biochem. 165:215–219] was developed. 2-Deoxyribose was purchased form Sigma Chemical Co. All other chemicals for the assay were purchased from BDH Chemicals Ltd. Degradation of deoxy ribose was achieved bv a mixture of $Fe^{2+}$, EDTA, ascorbic acid and $H_2O_2$. Reaction mixtures had a final volume of 1.0 ml and included the following reagents: 2-deoxyribose (18 mM) in HEPES buffer pH=7.2 (50 mM), ferrous ammonium sulfate (100 mM) EDTA (100 mM) and ascorbic acid (100 mM). The reaction mixture was incubated for 1 h at 37° C. Scavenging of hydroxyl radical was done by various concentrations of AMTP (compound C), and color was developed by reaction with thiobarbituric acid as described [Halliwell, B. et al., ibid.]

Hydroxyl radical chemiluminescence method

Chemiluminescence (CL) was measured in mixtures of $H_2O_2$, NTA-$Fe^{2+}$ and HRP (Horseradish peroxidase) systems in a LUMAC/3M BIOCONTER M2010 connected to a linear recorder as described [Ginsburg, I. et al. (1993) Inflammation 17:227–243]. The scavenging of hydroxyl radicals was done by various concentrations of AMTP (compound C dissolved in reaction buffer).

Superoxide radical assay

Superoxide radicals were produced from reactions of xanthine/xanthine oxidase [Mccord, J. M. and Fridovich I. (1969) J. Biol. Chem. 244:6049–6055]. The enzyme unit was adjusted to produce a linear flux of superoxide radicals which gave a slope of 0.12 OD/min at 550 nm. by reduction of cyt-C.

BSA Oxidation

BSA (0.5 mg/ml) in a 1 ml HEPES Buffer pH=7.2(50 mM) was incubated for 15 min with 1 mM sodium hypochlorite. Various concentrations of AMTP (compound B) were added to protect the protein. The sample was diluted in 3 ml of HEPES buffer and fluorescence was measured ($l_{ex}$=280 nm, $l_{em}$=345 nm) in a JASCO FP-770 spectrotluo-rometer. Fluorescence decav was due to tryptophan and tyrosine oxidation. Alternatively, BAS (0.5 mg/ml) in HEPES buffer (1 ml) was incubated with 2,2'-azobis-(2-amidinopropane)-HCL (AAPH) (a water soluble peroxy radical initiator) (50 mM) at 37° C. for a period of 4 h. The sample was diluted with 2 ml of the buffer and fluorescence was measured [Hazell, L. and Stocker, R. (1993) Biochem. J. 290:165–172].

BSA's Cystine Oxidation

BSA (0.5 mg/ml) in Imi HEPES buffer pH=7.2(50 mM) was incubated with sodium hypochlorite (1 mM) for 15 min. The protein was dialyzed for 2 h against 2×500 vol of HEPES buffer to remove free sodium hypochlorite. 301

DTNB 0.015 M in water was then added to the protein solution and color was measured at 420 nm. AMTPs were added to the protein sample to protect it against sodium hypochlorite [Hazell and Stocker, ibid.].

Pro-oxidative effect

Oxygen consumption from solutions that contained AMTPs or other antioxidants such as cystine or ascorbic acid at 10 mM each, and copper sulfate 10 mM, was monitored by Biological Oxygen Monitor, model YSI 53.

Liposomes Preparation

SUV liposomes were prepared from egg lecitin at 10% lipid concentration in a 50 ml HEPES buffer pH=6.9 according to already published procedures [Lichtenberg, D. and Barenholz. Y. (1988) Methods of Biochemical Analysis 33:337–462].

Intra lipid commercial emulsion (20%) was used as another model for lipid Oxidation.

Monitoring Lipid hydroperoxides

Lipid hydroperoxides were monitored by a modified micromolar sensitive spectroscopic method [Siddiqi, A. M. and Tappel, A. L. (1955) Chemist Analyst 44:52]. 50λ of lipids (liposomes or emulsion) were dissolved in 1 ml ethanol. 50λ of 50% potassium iodide solution were then added and the mixture was incubated for half an hour in the dark. The developed color was read in a spectrophotometer at 400 nm.

Thiobarbituric Acid Reactive Species assay for Lipids

The same procedure as described above for deoxyribose assay for hydroxyl radical was used for TBARS determination. Instead of deoxy ribose, 1% lipid was used. TBARS amounts were evaluated by florescence intensity reading at $\lambda_{ex}$=500; $\lambda_{em}$=554 [Halliwell and Gutteridge, ibid.].

Neutrophils activation determination

Human neutrophils (PMNs) were isolated from freshly drawn human blood according to already published procedures [Ginsburg et al., ibid.].

Chemiluminescence was measured in activated PMNs at 37° C. in a LUMAC/3M BIOCONTER M2010 connected to a linear recorder. PMNs ($3*10^5$–$2*10^6$/ml) were pipetted into plastic cuvettes, containing 1 ml HBSS, luminol ($5*10^{-5}$ M) and washed Streptococci 20 μl/ml (ten milliliters of a saline-washed suspension of group A Streptococci type 3 strain C203S of an optical density of 5.0 at 550 nm that was treated for 15 min at 37° C. with 100 μg/ml of poly L-histidine (PHSTD)HCL mol wt 23,000). The cationized suspension was then washed in normal saline and resuspended to the original volume. The cuvettes were mixed over a mechanical vortex and the chemiluminescence was immediately monitored until the peak CL was reached.

Modulation of chemiluminescence response was achieved by employing AMTP (compound B) molecules in various concentrations.

Culture cell

Human skin fibroblasts were kindly supplied by the Department for Human Genetics at Hadassa Hospital in Jerusalem. The cells were grown in D-MEM medium supplemented with glutamine, penicillin, and streptomycin and 10% fetal calf serum [Ginsburg, I. et al. (1992) Inflammation 16:519–538]. Radiolabeled cell monolayers were prepared by the addition of 10 μCi/ml of [$^{51}$Cr]NaCrO$_4$ (New England Nuclear) to 100 ml of trypsinized cells grown in 75-ml tissue culture bottles. The cells were then dispensed into 24-well tissue culture plates (Nunc, Roskilde, Denmark) and grown to confluency in a $CO_2$ incubator.

Reagents

Hydrogen peroxide flux was generated by the addition of glucose oxidase (0.5 units/ml) to the tissue culture media. Streptolysin S (SLS) of Croup A Streptococci (17 hemolytic units/ml) was employed as a membrane damaging agent.

Chromium release assay

Culture monolayers were treated for 1 h with the agents listed above. The cultures were monitored periodically for changes in cell morphology. To assess cytotoxicity, the supernatant fluids were removed and centrifuged at 2000 rpm for 2 min. The solubilized radioactivity was then determined in a Contron gamma counter. The total radioactivity associated with untreated controls was solubilized by the addition of 1 ml of 1% Triton X-100. (AMTPs influence on SLS hemolytic activity and on glucose oxidase activity was also tested. No influences were observed).

Results

Toxicity study

The toxicity of compound B was tested by injecting 75 mg/kg, 150 mg/kg, 300 mg/kg, 500 mg/kg, 700 mg/kg and 1000 mg/kg i.p. to groups of eight Sabra mice. The $LD_{50}$ was found to be around 700 mg/kg. No mortality was observed at doses up to 500 mg/kg nor were there any significant changes in the average weight of the mice in comparison to a saline injected control group after monitoring of 30 days. A repetitive i.p. injection of 75 mg/kg/day which was conducted on eight mice over a period of two weeks did not lead to any mortality or weight differentiation compared to the control.

$^{31}$P NMR study of AMTPs

Figure 2:
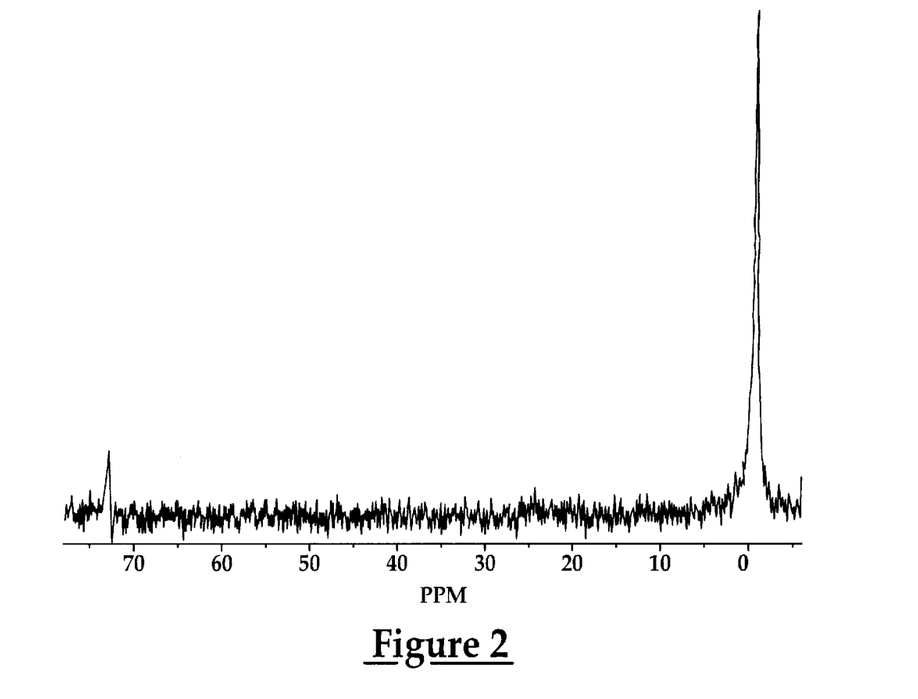

SUV liposomes (125 mM with 5 mM of compound B) were monitored for $^{31}$P (FIG. 2). The NMR spectrum showed complete separation between the chemical shifts of AMTP 73.036 ppm compounds and lecithin −0.467 ppm (probably also differ from other natural biological phosphates-containing molecules).

Scavenging effects

Compound B (5 mM in water) was introduced into 6 mM sodium hypochlorite. NMR spectrum was recorded immediately after the exposure to the hypochlorite and showed a single peak at 9.283 ppm (FIG. 3). The chemical shift indicated a complete oxidation of the sulfur group attached to the phosphate and its replacement with oxygen.

Figure 4:
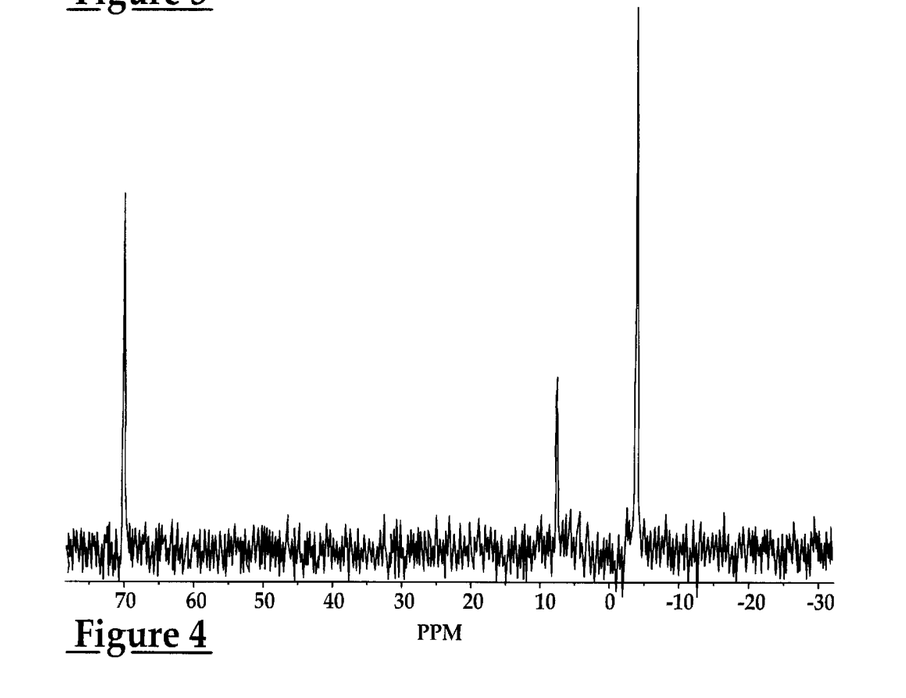

Compound B (5mM) was also decomposed by $H_2O_2$ (100 mM) with a rate dependent upon the environment and the dielectric constant. Two products of oxidation were observed by $^{31}$P NMR (FIG. 4). One product at 9.106 ppm and the other at −3.556 ppm. The second product indicated another fragmentation in the molecule.

Figure 5:
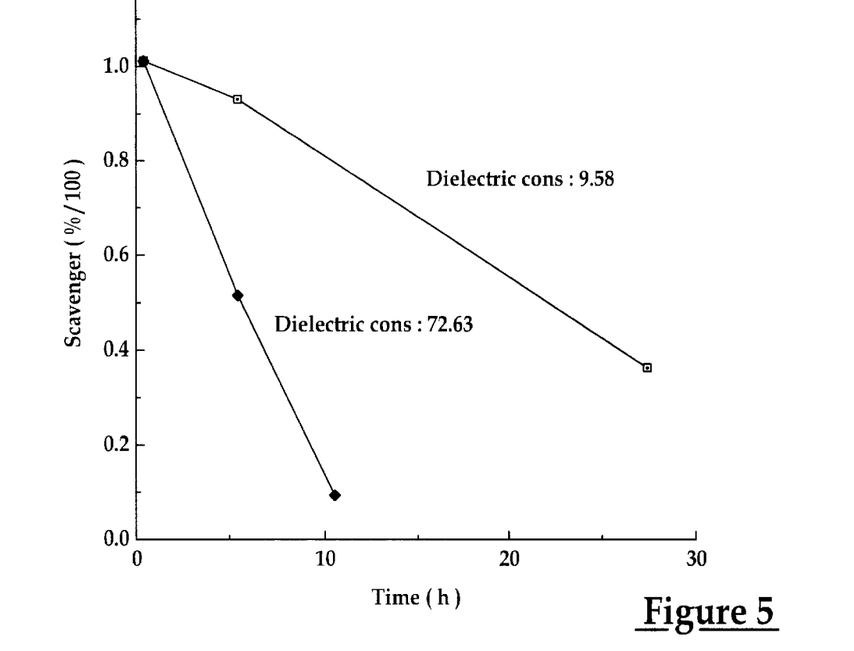

Different reaction rates were recorded by NMR kinetics between hydrogen peroxide and compound B either in a more hydrophilic environment and in a more hydrophobic one (different mixtures of 1,4-dioxane and water) with dielectric constants of 72.63 and 9.58 respectively. The reaction rate was much faster in high dielectric constants (FIG. 5).

Reaction of AMTP with different ROS

Scavenging of hydroxyl radicals

Figure 6:
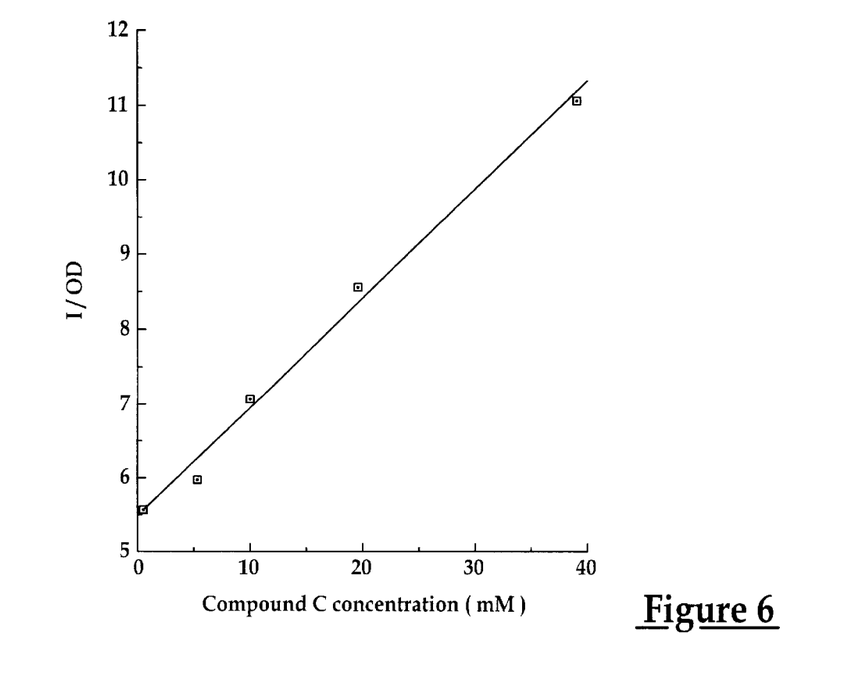
Figure 7:
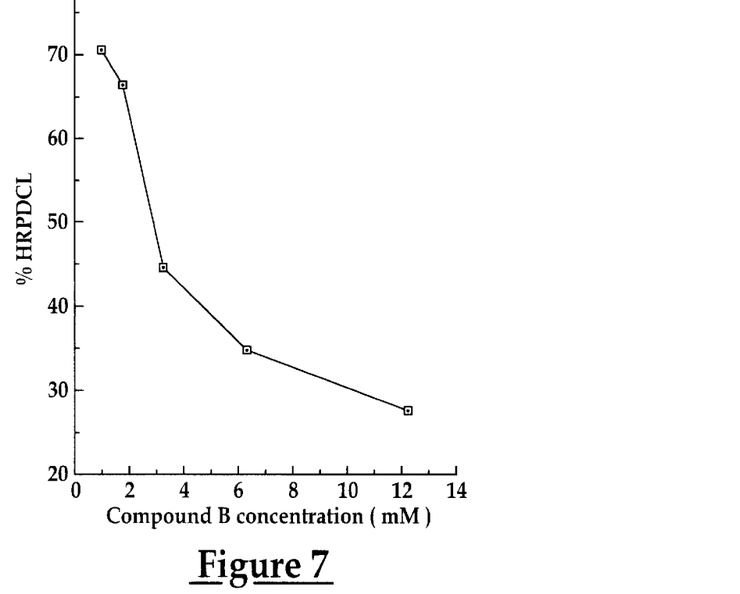

The scavenging of hydroxyl radicals by AMTPs was measured by two different methods in the first method compound C was found to be potent hydroxyl radical scavengers (FIG. 6). Equivalent concentrations of AMTP and deoxyribose significantly prevent deoxyribose degradation by hydroxyl radicals. The reaction rate constant of hydroxyl radicals with compound C was calculated from equation 1 and was found to be $1.5\times10^9$ $M^{-1}S^{-1}$.

$$A^{-1}=A_0^{-1}\{1+K[S]k(K_{DR}[DR])^{-1}\} \qquad \text{Equation 1}$$

where A is the absorbance in the presence of a scavenger S (AMTPs) at a concentration [S] and $A_0$ is the absorbance in the absence of a scavenger $K_{DR}=3.1*10^9$ (reaction constant between deoxyribose and OH. radical) [Ebert, M., et al. (1965) Pulse Radiolysis, Academic Press, London] and [DR]=18 mM. In the second method Chemiluminescence of OH. radical production by $H_2O_2$ and $Fe^{2+}$—NTA with horseradish peroxidase (HRP) was tested against compound B. Dose dependent decay of light was observed with increasing concentrations of compound B (FIG. 7). Considering the fast reaction between $H_2O_2$ and $Fe^{2+}$—NTA and the slow reaction rate between AMTP and hydrogen peroxide as monitored in the $^{31}P$ experiments (FIG. 5), the light decay may be exclusively attributed to hydroxyl radical scavenging.

Superoxide radical scavenging

Figure 8:
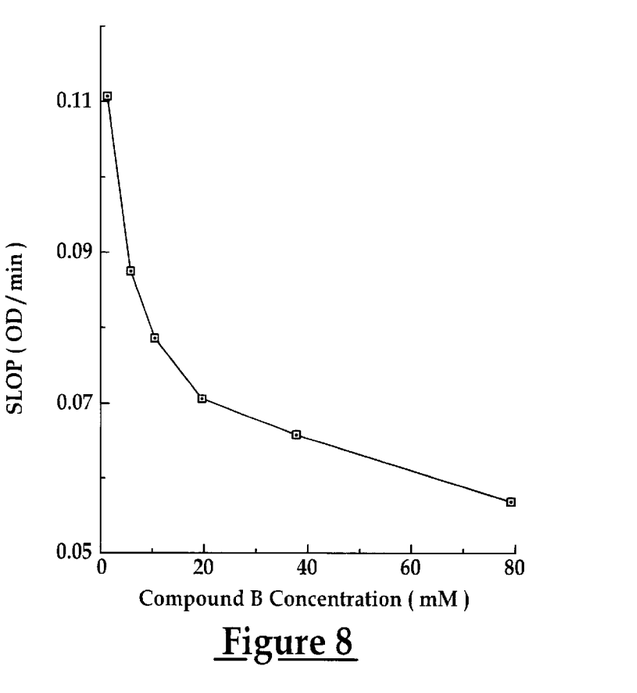

Superoxide radicals were produced by the xanthine/xanthine oxidase system, and the prevention of cyt C reduction by compound B was measured (FIG. 8). Compound B by itself did not reduce cyt C. The spontaneous second order reaction rate constant of superoxide with compound B was calculated from the initial slope to be $8.1*10^2$ $M^{-1}S^{-1}$.

Antioxidants effects of AMTP

Prevention of lipid peroxidation (initiation phase)

Figure 9:
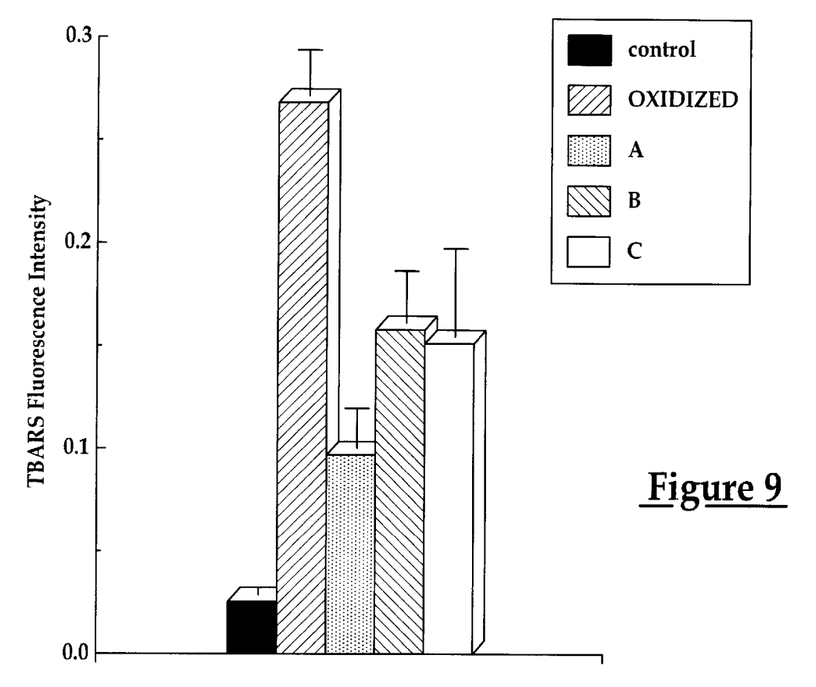

Lipid peroxidation was measured after the initiation of hydroxyl radicals in 1% emulsions by $Fe^{2+}$ (100 μM) vit C (100 μM) and $H_2O_2$ (1 mM). After 1 h of incubation amounts of thiobarbituric reactive species were measured. AMTPs added at concentrations of 10 mM inhibited the accumulation of thiobarbituric reactive species (FIG. 9). The more lipophilic the compound, the better it was in preventing peroxidation.

Figure 10:
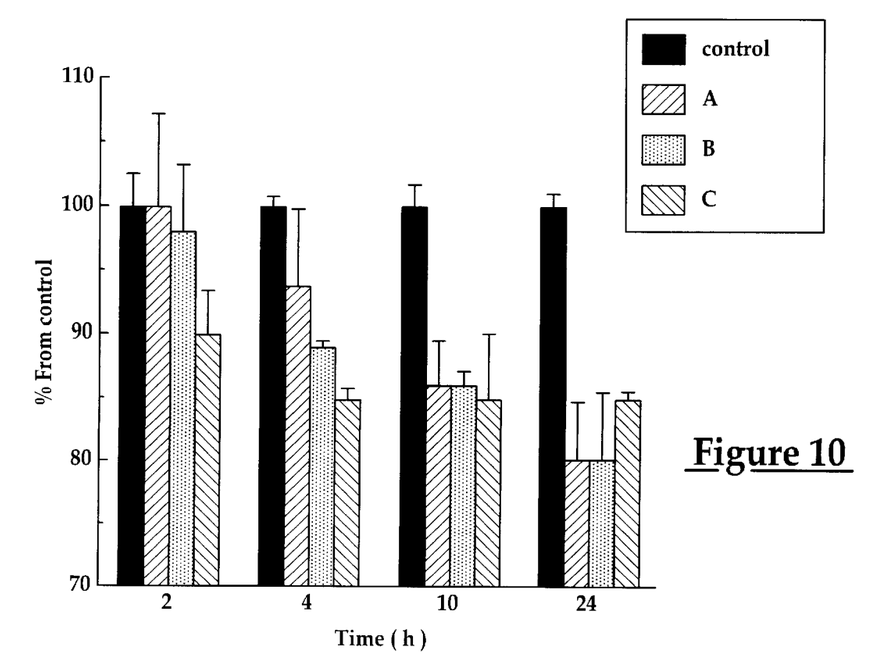

SUV Liposomes (12.5 mM) with certain degrees of oxidation were incubated with 5 mM AMTP molecules for period of 24 h. Peroxidation number (PN) was measured with potassium iodide in ethanol. AMTPs were able to decompose lipid hydroperoxide and to reduce the peroxidation number (PN). Compound C was more efficient in the first few hours of the incubation time with the liposomes but after 24 h the more lipophilic compounds of A and B were more effective in reducing PN (FIG. 10).

Prevention of protein oxidation

Figure 11:
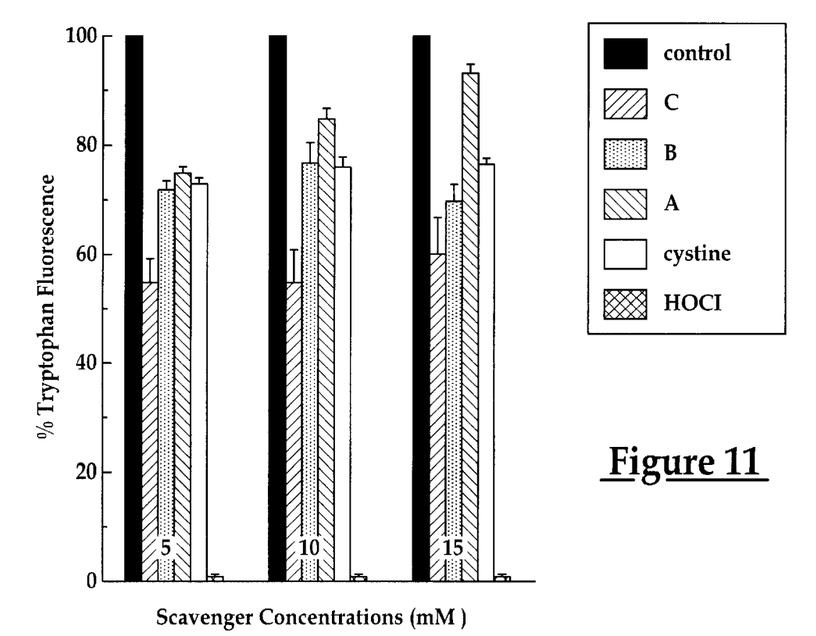
Figure 12:
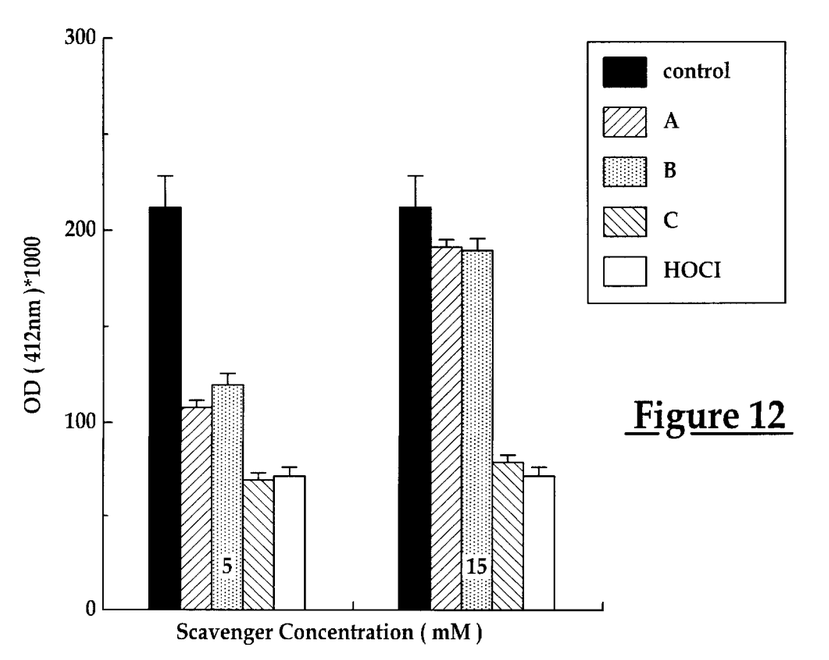

BSA's tryptophan oxidation and BSA's cystine oxidation were the models for protein damage by NaOCl (FIG. 11 and FIG. 12 respectively). BSA fluorescence intensity decreased following oxidative stress of NaOCl (1 mM). AMTPs molecules showed strong protection of fluorescent amino acid residues on the protein (tryptophan and tyrosine). Out of the three AMTP compounds the most lipophilic (A) was best in preventing the damage and provided 94% protection on the protein. AMTPs also showed the same defense profile on BSA's cystines when strong protection was induced by the more lipophilic compounds (A and B). These results may mean that the more lipophilic AMTP molecules protects the BSA lipophilic amino acid residues (tryptophan and cystine) by site specific defense mechanisms due to hydrophobic interaction with the protein and higher local concentration surrounding it.

Pro-Oxidative effects of AMTPs

AMTP molecules (10 mM) were incubated at pH=7.2 37° C. with $Cu^{2+}$ (10 mM). Oxygen consumption from the solution was measured with a Clark electrode (biological oxygen monitor). No oxygen consumption was observed from the solution. Ascorbic acid and cystine at equimolar concentrations produced a significant oxygen consumption (Table 1). The oxygen consumption rate is referred to free radical production rate.

TABLE 1

| Pro-Oxidative Effects | | | |
|---|---|---|---|
| $CU^{2+}$ | $AMTP/CU^{2+}$ | $Cys/Cu^{2+}$ | vit $C/Cu^{2+}$ |
| NOC | NOC | $2.35*10^{-6}$ | $2.87*10^{-5}$ |
|  |  | $(0.625*10^{-6})$ | $(0.24*10^{-5})$ |

NOC = No oxygen consumption.
[vit C] = 10 mM
$[Cu^{+2}]$ = 10 mM
[Cys] = 10 mM
Rate of oxygen consumption in M/min.

Cell experiments

Figure 13:
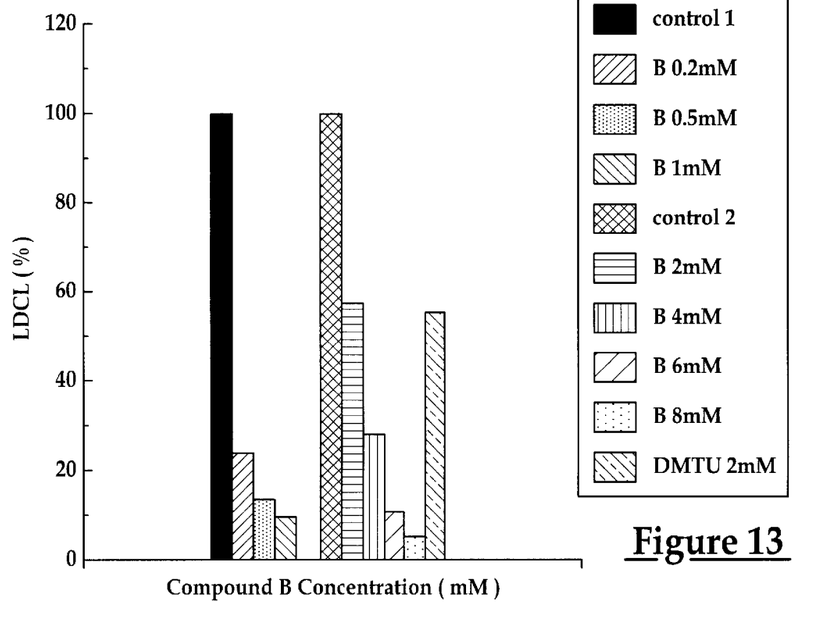

Modulation of chemiluminescence in activated neutrophils by ASMTPs Neutrophils were activated in 1 cc of HBSS by a suspension of cationized streptococcus under the effect of various concentrations of compound B. A dose dependent reduction of light emission by compound B via free radical scavenging was monitored by a chemiluminator (FIG. 13). Two experiments were done. In the first experiment with $3-4*10^5$ cells/ml, a concentration of less than 1 mM of compound B was required to quench 90% of light production. Control 1 in FIG. 13 represents neutrophils treated with streptococcus alone (14,000–17,000 light units at the peak), Spontaneous light production measurements were 1,400–2,000 light CPM. In the second experiment Control 2 represents $1.5*10^6$ cells per 1 ml HBSS activation of the cells by cationized streptococcus produced between 50,000–63,000 light units at the peak. 8 mM of compound B reduced the light measurements to the base level of 3500 light units.

Fibroblast cells cultures

Figure 14:
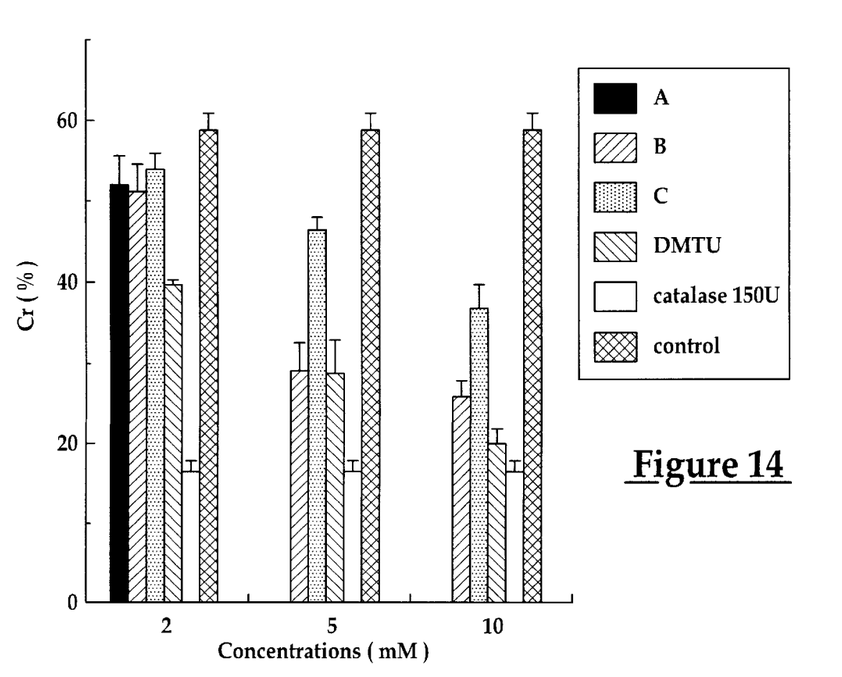

Fibroblasts in culture were exposed to a synergistic killing mechanism (streptolysin S in combination with an oxidant glucose oxidase) in a D-MEM culture medium that contained 1 mg/ml of glucose (about 0.5–1 mM of $H_2O_2$ was produced after 1 hour of incubation at 37° C.). This system caused about 60% chromium released within an hour. Compounds B and C themselves did not show any toxic effects on the cell at concentrations of up to 20 mM but were able to induce 50–60% protection against cell killing at concentrations up to 10 mM (FIG. 14). Compound A was not soluble in the D-MEM medium at concentrations above 2 mM but showed a protection of 10% at this concentration (FIG. 14). The positive controls were DMTU and catalase.

What is claimed is:

1. A pharmaceutical composition in a solid dosage form suitable for oral administration that comprises the compound 2-hydroxyethylamido diethylthionophosphate in a pharmaceutically acceptable carrier.

2. A pharmaceutical of claim 1, wherein the dosage form affords prolonged and sustained release.

* * * * *